United States Patent [19]

Studer

[11] Patent Number: 5,179,129

[45] Date of Patent: Jan. 12, 1993

[54] STAGED LIQUID PHASE METHANOL PROCESS

[75] Inventor: David W. Studer, Wescosville, Pa.

[73] Assignee: Air Products and Chemicals, Inc., Allentown, Pa.

[21] Appl. No.: 664,178

[22] Filed: Mar. 1, 1991

[51] Int. Cl.$^5$ .................. C07C 27/06; C07C 27/08
[52] U.S. Cl. .................... 518/700; 518/706
[58] Field of Search .................... 518/700, 706

[56] References Cited

U.S. PATENT DOCUMENTS

| | | |
|---|---|---|
| 2,467,802 | 4/1949 | Barr . |
| 2,852,350 | 9/1958 | Kolbel et al. ............... 23/288 |
| 4,540,712 | 9/1985 | Dombek ..................... 518/700 |
| 4,608,818 | 9/1986 | Goebel et al. ............... 60/39.12 |
| 4,665,688 | 5/1987 | Schiffers et al. ............ 60/39.07 |
| 4,766,154 | 8/1988 | Bonnell et al. .............. 518/700 |
| 4,946,477 | 8/1990 | Perka et al. ................ 48/197 |

Primary Examiner—Howard T. Mars
Attorney, Agent, or Firm—John M. Fernbacher; James C. Simmons; William F. Marsh

[57] ABSTRACT

Methanol is produced from synthesis gas comprising hydrogen, carbon monoxide, and carbon dioxide in a two-stage liquid phase reactor system. Each reactor is operated in an optimum temperature range to maximize methanol productivity, and once-through product conversion of up to 9.1 moles methanol per 100 moles of synthesis gas can be achieved with reasonable catalyst utilization. Overall catalyst utilization is increased by countercurrent catalyst transfer. In an alternate mode of operation, the liquid phase reactor system is integrated with a coal gasification combined cycle (CGCC) power generation process wherein the unreacted synthesis gas is used as fuel in a gas turbine-driven electric power generator. Operation of each liquid phase reactor in the optimum temperature range maximizes the available heat of reaction which is recovered as steam; the steam is utilized in the gas turbine combustor or the CGCC steam turbine. Methanol from the liquid phase reactor system can be used as peak shaving fuel for the gas turbine.

14 Claims, 4 Drawing Sheets

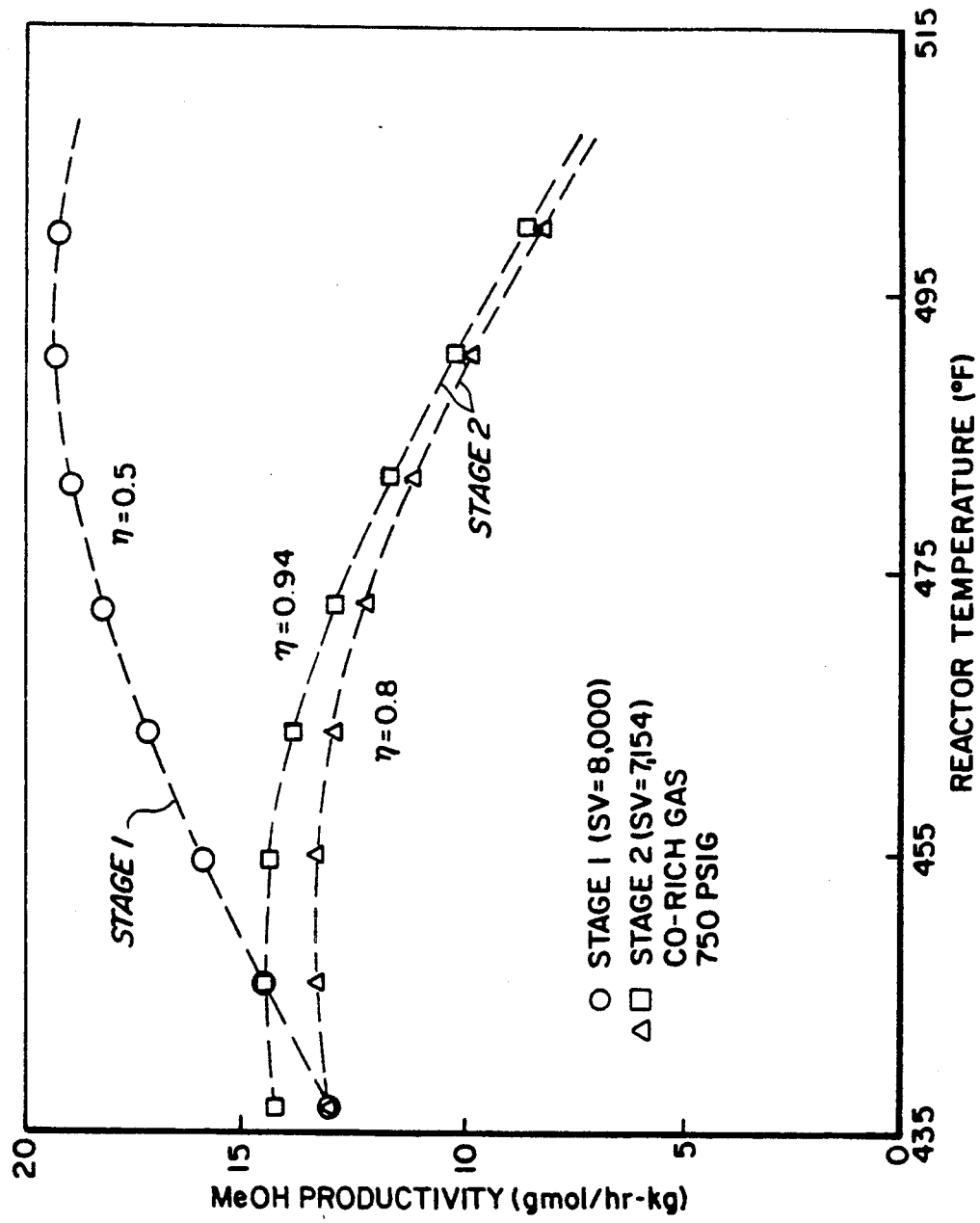

STAGED LIQUID PHASE METHANOL PROCESS

FIELD OF THE INVENTION

This invention pertains to the production of methanol from synthesis gas, and in particular to the production of methanol in a staged liquid phase reactor system.

BACKGROUND OF THE INVENTION

Methanol is produced commercially from synthesis gas comprising hydrogen, carbon monoxide, and carbon dioxide by contacting the synthesis gas with a solid methanol synthesis catalyst in one or more gas phase synthesis reactors. Most of the world's methanol is produced by this reaction route utilizing the well-known Lurgi and ICI methanol synthesis processes. An improved methanol synthesis process which utilizes powdered catalyst mixed with an inert liquid, known as the liquid phase methanol process, is disclosed in U.S. Pat. Nos. 3,888,896, 4,031,123, and 4,567,204. This process operates more efficiently than the gas phase process because the heat of reaction is absorbed by the inert liquid thus allowing closer temperature control in the reactor; heat is removed from the inert liquid in a separate cooling step. As a result of closer temperature control, a higher per pass conversion to methanol can be achieved with the liquid phase process than with conventional gas phase reactor systems. The liquid phase methanol process can utilize a much wider range of synthesis gas compositions than gas phase processes, and is particularly useful for CO-rich synthesis gas such as that produced by the coal gasification processes. Further improvement in operating efficiency and methanol yield in the liquid phase process can be realized by using multiple stages as disclosed in U.S. Pat. No. 4,766,154, the specification and drawings of which are incorporated herein by reference. This process utilizes a two-stage slurry reactor system which is operated such that a specific reaction mechanism occurs in each reactor; in the first stage reactor, the operation is controlled to favor the hydrogenation of carbon monoxide, while in the second stage reactor the operation is controlled to favor the hydrogenation of carbon dioxide. The staged process results in substantial increases in methanol yield over a single-stage liquid phase process. The staged process comprises feeding synthesis gas containing hydrogen, carbon monoxide, and carbon dioxide into the first stage reactor, withdrawing a stream containing methanol and unreacted synthesis gas components, cooling the stream and recovering methanol product therefrom, passing the unreacted synthesis gas components into the second stage reactor, and recovering additional methanol product from the second stage reactor effluent stream. Unreacted synthesis gas components are recycled to the inlet of the second stage reactor. Heat is removed from the inert liquid of each reactor by withdrawing a portion of the inert liquid as a slurry, cooling the slurry in an external heat exchanger, and pumping the cooled slurry back into the reactor.

U.S. Pat. No. 2,467,802 discloses a staged, gas-phase fluidized bed process for converting synthesis gas containing hydrogen and carbon oxides into hydrocarbons and oxygenated organic compounds. The process comprises passing synthesis gas upward through a series of fluidized catalyst beds, forming product components in each of the beds, and withdrawing product and unreacted synthesis gas from the last stage reactor. The volume and diameter of each reactor stage decreases in the direction of gas flow. Fresh catalyst is introduced into the last stage reactor and is partially spent therein; the catalyst then flows through one or more additional beds in series in a countercurrent direction to the synthesis gas flow, and finally spent catalyst is removed from the first stage reactor. Preferably, reaction products are removed from the gas stream between each stage and the unreacted synthesis gas is passed into the next stage. Heat is removed from each stage by a cooling coil installed in each reactor. As a result of the countercurrent flow of gas and catalyst, and the changing of the sizes of the reactor stages in the direction of gas flow, the optimum conditions of pressure, temperature, and gas velocities may be approximately the same in all reactor stages.

U.S. Pat. No. 2,852,350 discloses a reactor for the production of hydrocarbons from hydrogen and carbon monoxide in a slurry reactor in accordance with the Fisher-Tropsch process. The reactor consists of a pressure vessel containing a multiple number of internal vertical bundles of cooling tubes wherein the bundles are arranged such that the effective number of tubes and thus the effective heat transfer surface area decreases in the direction of gas flow. Gas flows upward through a catalyst slurry on the shell side of the tubes while coolant flows within the tubes.

A medium-load power generating plant with an integrated coal gasification plant is disclosed in U.S. Pat. No. 4,608,818. During periods of low power requirements excess synthesis gas is converted to methanol in parallel gas-phase methanol synthesis reactors. One of these methanol synthesis reactors is operated in a once-through mode and the unreacted synthesis gas is returned to the plant synthesis gas handling system. In the remaining methanol synthesis reactors the unreacted synthesis gas is recycled as reactor feed.

U.S. Pat. No. 4,665,688 discloses a power generating plant with an integrated coal gasification plant which produces synthesis gas, one portion of which is fired in a gas turbine power generation system and the remainder of which is used to produce methanol and other chemical products such as acetic acid. Unreacted synthesis gas from the methanol and acetic acid reactors is utilized for gas turbine fuel.

U.S. Pat. No. 4,946,477, the specification and drawings of which are incorporated herein by reference, discloses an improved integrated coal gasification combined cycle power generation process including once-through methanol production from the synthesis gas provided by the gasifier. Unreacted synthesis gas is utilized in a gas turbine generator to produce power. The improvement comprises utilizing a liquid phase methanol synthesis reaction system, a portion of the unreacted synthesis gas from which is separated into a hydrogen-rich stream and a CO-rich stream; the CO-rich stream is used as gas turbine fuel. The remainder of the unreacted synthesis gas is combined with the hydrogen-rich stream, $CO_2$ is removed from the combined stream, and the resulting stream feeds a gas-phase methanol reactor to produce additional methanol. Unreacted synthesis gas from this reactor is used as gas turbine fuel.

The liquid phase reaction process is an efficient method for the production of methanol from synthesis gas, and particularly CO-rich synthesis gas. When synthesis gas is obtained by gasifying coal, the composition of the gas may vary over time due to changes in coal feedstock properties and gasifier operating conditions. In particular, the concentration of certain compounds which reduce the activity of the catalyst may change with time, thus in turn affecting the optimum operation of the process. Changes in the relative amounts of hydrogen and carbon oxides in the synthesis gas further affect the optimum operation of the process. The present invention as disclosed and claimed below addresses these problems and teaches an improved method of operating liquid phase methanol reactors and integrating the reactors with a coal gasification combined cycle power generation system.

SUMMARY OF THE INVENTION

The present invention is a process for the production of methanol from synthesis gas comprising hydrogen, carbon monoxide, and carbon dioxide by reaction in a series of at least two liquid phase methanol reactors. The synthesis gas is introduced into a first liquid phase reactor which contains a solid methanol synthesis catalyst in an inert liquid, and methanol is produced therein. An effluent gas stream comprising methanol, hydrogen, carbon monoxide, and carbon dioxide is withdrawn from the first reactor and introduced into a second liquid phase reactor which contains the same type of solid methanol synthesis catalyst in the same type of inert liquid, wherein additional methanol is produced, and a mixed product stream is withdrawn from the second reactor. Heat is removed from the first and second liquid phase reactors to control the respective temperatures therein such that the methanol productivity is maximized for a given composition of the synthesis gas feed and the given activity of the catalyst in each of the reactors. This heat is removed by indirect heat exchange with synthesis gas feed, steam, or boiler feedwater in a first and a second heat exchanger located respectively within the first and second reactors.

Catalyst inventory and activity are maintained in the reactors by withdrawing spent catalyst from the first liquid phase reactor, transferring partially spent catalyst from the second liquid phase reactor to the first liquid phase reactor, and introducing fresh catalyst into the second liquid phase reactor. Alternately, fresh catalyst can be introduced individually into a given reactor and spent catalyst can be withdrawn individually from the given reactor.

Vaporized inert liquid in the mixed product stream is condensed, separated, and recycled to the first and second reactors. The mixed product stream, essentially free of vaporized inert liquid, is further separated into a crude methanol product and unreacted synthesis gas components comprising hydrogen, carbon monoxide, and carbon dioxide.

An alternate mode of the invention is an integrated process for the coproduction of methanol and electric power in a coal gasification combined cycle system. Coal is gasified to produce a crude synthesis gas comprising hydrogen, carbon monoxide, carbon dioxide, sulfur-containing impurities, and particulates; the sulfur-containing impurities and particulates are removed to yield a synthesis gas feed comprising hydrogen, carbon monoxide, and carbon dioxide. A first portion of the synthesis gas feed is introduced into a first liquid phase reactor containing a solid methanol synthesis catalyst in an inert liquid wherein the first portion of synthesis gas feed reacts in the presence of the catalyst to produce methanol. A sufficient amount of heat is removed from the first liquid phase reactor to control the temperature therein such that the methanol productivity is maximized for a given composition of synthesis gas feed and a given activity of the catalyst. This sufficient amount of heat is removed by indirect heat exchange between boiler feedwater and the inert liquid thereby generating a first stream of steam. An effluent gas stream comprising methanol, hydrogen, carbon monoxide, and carbon dioxide is withdrawn from the first liquid phase reactor and is introduced into a second liquid phase reactor containing the same types of methanol synthesis catalyst and inert liquid as in the first reactor, and the effluent gas stream reacts in the presence of the catalyst to produce additional methanol. A sufficient amount of heat is removed from the reactor to control the temperature therein such that the methanol productivity is maximized for a given composition of the effluent gas stream and a given activity of the catalyst. This sufficient amount of heat is removed by indirect heat exchange between boiler feedwater and the inert liquid thereby generating a second stream of steam.

A mixed product stream comprising methanol, hydrogen, carbon monoxide, and carbon dioxide is withdrawn from the second liquid phase reactor and is separated into a crude methanol product and a stream of unreacted synthesis gas comprising hydrogen, carbon monoxide, and carbon dioxide. A second portion of the synthesis gas feed is combined with at least a portion of the unreacted synthesis gas and the combined stream is introduced into the combustor of a gas turbine-driven electric generator which is part of the coal gasification combined cycle system, thereby generating electric power. Energy from the first and second streams of steam is recovered by injecting the steam into one or more subsystems of the coal gasification combined cycle system, namely the gas turbine combustor, the steam turbine, and a utility steam system. At least a portion of the crude methanol product is utilized as fuel in the gas turbine combustor.

The invention is also a reactor system for the production of methanol from synthesis gas feed containing hydrogen, carbon monoxide, and carbon dioxide which includes a first reactor comprising a first vessel containing a solid methanol synthesis catalyst in an inert liquid; means for introducing a synthesis gas feed stream into the first vessel; means for introducing the solid methanol synthesis catalyst and the inert liquid into the first vessel; means for withdrawing an effluent gas stream from the first vessel; means for withdrawing at least a portion of the solid methanol synthesis catalyst and inert liquid from the first vessel; first heat exchange means for removing heat from the contents of the first vessel; and first control means to regulate the amount of heat removed from the contents of the first vessel in order to control the temperature therein at a predetermined value. The reactor system further includes a second reactor comprising a second vessel containing the same solid methanol synthesis catalyst in the same inert liquid; means for transferring the effluent gas stream from the first vessel into the second vessel; means for introducing the solid methanol synthesis catalyst and the inert liquid into the second vessel; means for withdrawing a mixed product gas stream from the second vessel; means for withdrawing at least a portion of the solid methanol synthesis catalyst and the inert liquid from the second vessel; means for transferring at least a portion of the solid methanol synthesis catalyst and the inert liquid from the second vessel to the first vessel;

second heat exchange means for removing heat from the contents of the second vessel; and second control means to regulate the amount of heat removed from the contents of the second vessel in order to control the temperature therein at a predetermined value.

Several advantages are realized in the present invention compared with prior art liquid phase methanol processes. First, because of the efficiency of staged operation, a significant increase in methanol production per unit of synthesis gas feed is obtained. Second, the catalyst utilization is improved, which increases the amount of methanol produced per unit of catalyst consumption compared with a single-stage reactor system. In addition, methanol losses in the unreacted synthesis gas (stream 77, FIG. 1 or stream 514, FIG. 3) are reduced because the flow rate of this stream is lower than the corresponding stream in a single-stage system. Further, the methanol concentration in the final reactor effluent (stream 505, FIG. 3) is higher for the two-stage operation than the single-stage operation, which allows higher product recovery. In the alternate mode of the invention, the total amount of available energy recovered from the first and second liquid phase reactors for utilization in the coal gasification combined cycle system is maximized by operating each of the liquid phase reactors in a temperature range which maximizes methanol productivity.

BRIEF DESCRIPTION OF THE DRAWINGS

FIG. 4 is a plot of methanol productivity vs reactor temperature for each stage of the reactor system of the present invention.

DETAILED DESCRIPTION OF THE INVENTION

Synthesis gas containing hydrogen, carbon monoxide, and carbon dioxide can be produced by the gasification of coal, by partial oxidation of hydrocarbons, or by steam reforming of light gaseous hydrocarbons. The process of the present invention can operate successfully over a wide range of synthesis gas feed compositions typical of such processes, and is particularly well-suited for the production of methanol from syngas having a high CO concentration obtained from coal gasification processes such as those developed by Texaco, Shell, and others.

Figure 1:
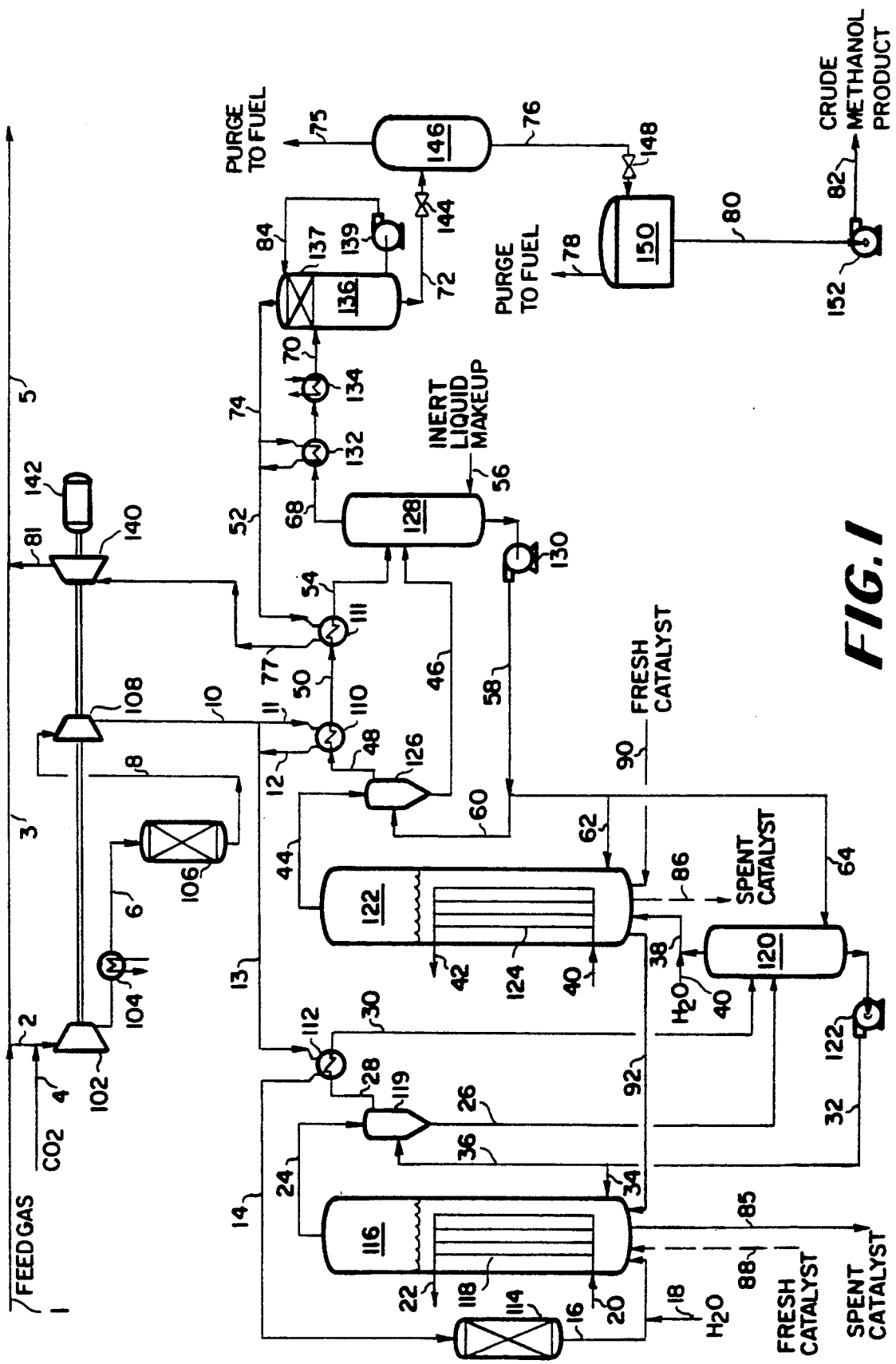
FIG. 1 is a flow diagram for the process of the present invention.

A schematic flowsheet for the process of the present invention is shown in FIG. 1. Synthesis gas feed comprising hydrogen, carbon monoxide, and carbon dioxide which is essentially free of solid particles and sulfur-containing compounds flows through lines 1 and 2, is compressed to between about 300 and 500 psig in compressor 102, and is cooled to between 80° and 120° F. in cooler 104. The compressed gas flows through line 6 into carbonyl guard bed 106 in which most of the iron and nickel carbonyl compounds, which poison the methanol synthesis catalyst, are removed. The syngas then flows through line 8 and is further compressed in second stage compressor 108 to between about 500 and 1500 psig. Optionally, at least a portion of compressed syngas stream 10, now between about 250° and 350° F., flows as stream 11 to heat exchanger 110 where it is further heated by indirect heat exchange with hot effluent stream 48 from separator 126. Stream 12 from exchanger 110 is combined with the remainder of stream 10 to form combined stream 13 which is further heated in heat exchanger 112. Syngas feed now at a temperature between about 325° and 430° F. passes through line 14 and into sulfur guard bed 114 in which hydrogen sulfide and carbonyl sulfide are adsorbed. Syngas feed finally passes through line 16 and into the first stage liquid phase methanol reactor 116. Water is optionally added to the reactor feed through line 18, which is particularly useful when the synthesis gas is high in CO. $CO_2$ is optionally added to the feed gas through line 4, which is particularly useful when the synthesis gas is low in $CO_2$. Liquid phase methanol reactor 116 contains a slurry of a powdered methanol synthesis catalyst suspended in an inert liquid; a commercial catalyst such as BASF S3-86 containing copper and zinc oxide on alumina can be used. The inert liquid can be selected from a number of commercially available organic liquids and hydrocarbon mineral oils, particularly those with a high paraffinic and/or naphthenic content. Preferred commercial products include Drakeol-10 sold by Penreco and Freezene 100 sold by Witco. Alternately, the catalyst can be used as pellets and each reactor operated as an ebullated bed, but operation in the fluidized bed mode with powdered catalyst is preferred.

The synthesis gas feed passes upward through the catalyst slurry and reacts exothermally to yield methanol. The heat of reaction is absorbed by the inert liquid and is removed by heat exchanger 118 to control the temperature in the first stage reactor between about 455° to 535° F., preferably between about 475° to 515° F. Cooling fluid stream 20 absorbs heat from the slurry by indirect heat exchange in heat exchanger 118 and the hot fluid flows from the reactor as stream 22. The cooling fluid can be cool synthesis gas feed, steam, boiler feedwater, or another process stream. The temperature in reactor 116 is controlled by a typical feedback control system which determines the average temperature of the catalyst slurry, compares this temperature with a selected set point, and utilizes the deviation from this set point to drive a flow control valve (not shown) which regulates the flow rate of either stream 20 or 22. Other control methods known in the art also can be used to control reactor temperature. Effluent gas stream 24, now containing methanol, unreacted synthesis gas components, a small amount of vaporized inert liquid, and a small amount of entrained slurry, passes into separator 119 where substantially all of the entrained slurry is removed as stream 26, which flows into separator 120. The remaining components in stream 28 flow through heat exchanger 112 and are cooled by indirect heat exchange with synthesis gas feed stream 13 to condense a fraction of the vaporized inert liquid originally in stream 28. Optionally, heat can be removed from the unreacted synthesis gas by a heat exchanger in the vapor space of the reactor (shown in FIG. 3). The cooled stream 30 flows into separator 120 where condensed inert liquid and previously entrained catalyst slurry are removed and returned via pump 122 to reactor 116 and separator 119. A portion of the slurry stream 32 is returned to reactor 116 as stream 34 and the remainder as stream 36 passes to separator 119 to aid in the separation of the entrained catalyst slurry in stream 24. Other control methods known in the art also can be used to control reactor temperature.

Unreacted synthesis gas components and gaseous methanol flow as stream 38 into the second stage liquid phase methanol reactor 122 which contains a slurry of a powdered methanol synthesis catalyst suspended in an inert liquid similar to that described for reactor 116. The unreacted synthesis gas components pass upward through the catalyst slurry and react exothermally to yield additional methanol. The heat of reaction is absorbed by the inert liquid and is removed by heat exchanger 124 to control the temperature in the second stage reactor between about 415° to 475° F., preferably between about 425° to 465° F. Cooling fluid stream 40 absorbs heat from the slurry by indirect heat exchange in heat exchanger 124 and the hot fluid flows from the reactor as stream 42. The cooling fluid can be cool synthesis gas feed, steam, boiler feedwater, or other process streams. Water is optionally added to the reactor feed stream 38 through line 40. The temperature in reactor 122 is controlled by a typical feedback control system which determines the average temperature of the catalyst slurry, compares this temperature with a selected set point, and utilizes the deviation from this set point to drive a flow control valve (not shown) which regulates the flow rate of either stream 40 or 42.

Product stream 44, now containing methanol, unreacted synthesis gas components, a small amount of vaporized inert liquid, and a small amount of entrained slurry, passes into separator 126 where substantially all of the entrained slurry is removed as stream 46, which flows into separator 128. The remaining components in stream 48 flow through heat exchanger 110 and are cooled by indirect heat exchange with at least a portion 11 of synthesis gas feed stream 10 to condense at least a portion of the vaporized inert liquid. The cooled stream 50 flows through heat exchanger 111 where it is further cooled by indirect heat exchange with stream 52 to condense essentially all of the remaining vaporized inert liquid, and the cooled stream 54 flows into separator 128 where condensed inert liquid and previously entrained catalyst slurry are recovered. Additional inert liquid makeup is introduced into separator 128 as needed via stream 56. The recovered slurry including inert liquid makeup is removed from the bottom of separator 128 and is returned to the reactor system as stream 58 by pump 130. The slurry in stream 58, typically containing about 0.5 to 2.0 weight % catalyst, is returned to one or more of the following locations: to separator 126 as stream 60, to reactor 122 as stream 62, and to separator 120 as stream 64. Crude product stream 68 is cooled and partially condensed by indirect heat exchange with a portion of unreacted synthesis gas stream 74 in heat exchanger 132 and also with cooling water in heat exchanger 134. Alternately, under certain process conditions, it may be advantageous to utilize stream 68 as feed to a third stage liquid phase reactor system (not shown) for further conversion to methanol. Cooled and partially condensed crude product stream 70 flows into separator 136 and crude methanol stream 72 is withdrawn from the bottom of the separator. Vapor stream 74 containing unreacted synthesis gas components is withdrawn from the top of separator 136, and at least a portion of stream 74 is heated in exchanger 132. The resulting heated stream 52 is further heated in exchanger 111 to yield stream 77. Optionally, separator 136 can include a short packed section 137, recirculation loop 84, and pump 139 to minimize inert liquid droplet carryover in vapor stream 74.

Crude methanol stream 72, which is typically at a temperature between 80° and 120° F. and a pressure between 450 and 1450 psia, contains dissolved unreacted synthesis components. In order to remove these components, stream 72 is flashed across valve 144 to a pressure of 50 to 100 psia and flows into separator 146 which yields an intermediate crude methanol liquid stream 76 and gas stream 75 suitable as fuel. Stream 76 is then flashed to near atmospheric pressure across valve 148 and flows into storage tank 150 where a final gas stream 78 is recovered for fuel. Crude methanol product is stored in tank 150 and is withdrawn when needed as stream 80. Pump 152 delivers the final crude methanol product as stream 82.

The process of the present invention can be integrated with a coal gasification combined cycle (CGCC) power generation system in which unreacted synthesis gas stream 77 is expanded in expander 140 and combined with a portion 3 of the synthesis gas feed stream 1; the combined stream 5 is combusted in a gas turbine which drives an electric generator. Work recovered in expander 140 is utilized with motor 142 to drive compressors 102 and 108. Purge streams 75 and 78 also can be used as fuel in the gas turbine. The process of the present invention can be heat integrated with the CGCC system by raising steam from the heats of reaction in reactors 116 and 122 and sending this steam to the CGCC steam turbine or alternately to the CGCC gas turbine combustor. This steam is obtained by introducing boiler feedwater through lines 20 and 40 into heat exchangers 118 and 124 respectively, and withdrawing steam therefrom as streams 22 and 42. At least a portion of crude methanol product stream 82 can be utilized as a peak shaving fuel for the CGCC gas turbine during periods of high power demand.

Management of catalyst inventories and activities in reactors 116 and 122 can be accomplished in several ways. The first entails the individual removal of spent catalyst from each reactor followed by the addition of fresh catalyst to each reactor in sufficient amounts to control the average catalyst activity at the desired level in each reactor. In this operating mode, spent catalyst is removed directly from each of the reactors via lines 85 and 86 respectively, and fresh catalyst is introduced into each of the reactors via lines 88 and 90 respectively. The catalyst is conveniently handled as a slurry with the selected inert liquid. An alternate and preferred method of managing catalyst inventories and activity levels is to remove spent catalyst through line 85 from the first stage reactor 116, transfer partially spent catalyst from the second stage reactor 122 via line 92 to reactor 116, and add fresh catalyst to second reactor 122 via line 90. Catalyst addition, transfer, and withdrawal can be accomplished either continuously or intermittently, and the amount of catalyst replaced in each reactor per day is between about 0.2 and 1.5 wt% of the total catalyst in that reactor. The total catalyst charge in a reactor varies between about 6,000 and 17,000 kg. The actual rate of catalyst addition, transfer, and withdrawal will depend on reactor operating conditions and the level of catalyst poisons in the synthesis feed gas.

The optimum temperature in a liquid phase methanol reactor is determined by a balance between the kinetic reaction rate, catalyst deactivation rate, and thermodynamic equilibrium. Higher temperatures yield higher kinetic reaction rates while lower temperatures result in thermodynamic equilibrium which favors higher methanol concentrations in the reactor product. Catalyst life is also important in determining the optimum temperature, since higher temperature causes a higher deactivation rate due to sintering and promotes deactivation due to surface reactions with impurities in the synthesis gas feed. Particular contaminants which deactivate the catalyst include iron carbonyl compounds, sulfur compounds, chlorides, and various metals. Reactor catalyst activity also influences the choice of the optimum temperature, since lower activity catalyst requires higher temperatures and higher activity catalyst requires lower temperatures for an equivalent methanol productivity. The optimum reactor temperature which yields the maximum conversion of synthesis gas to methanol according to the present invention is thus a complex function of several operating parameters, and cannot be predicted a priori from the prior art.

The staged liquid phase reactor system of the present invention as described above allows higher synthesis gas conversion to methanol and lower catalyst consumption compared with prior art processes. The following Examples describe typical operating conditions for the staged process of the present invention, compare the operation of the staged process with a single-stage liquid phase methanol process, and illustrate the benefits of temperature optimization in staged reactors.

EXAMPLE 1

Figure 2:
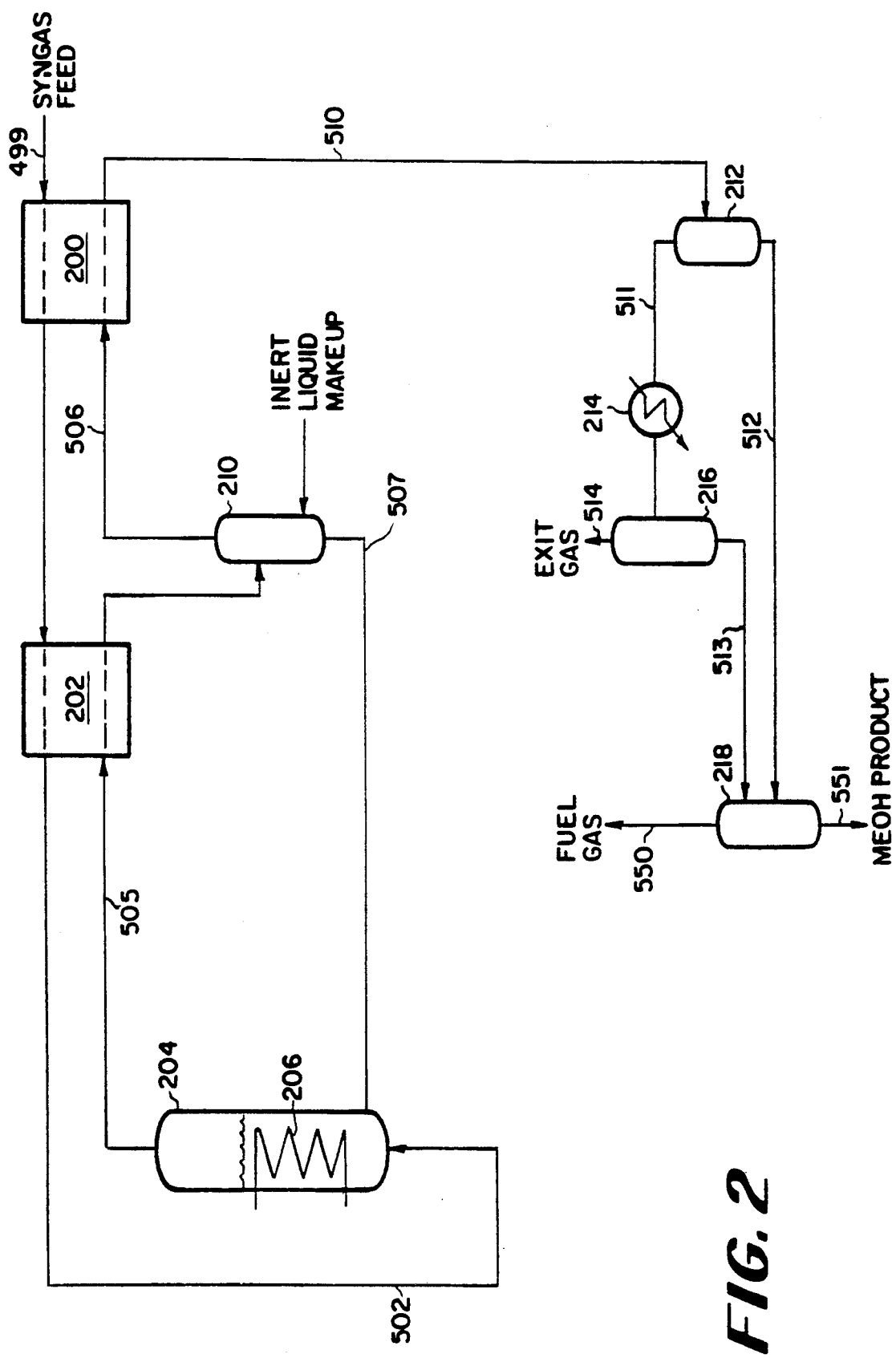
FIG. 2 is a simplified flow diagram for a single-stage liquid phase methanol process.

A process simulation was carried out for the single-stage liquid phase methanol process shown schematically in FIG. 2. Synthesis gas feed 499, typical of synthesis gas from the Texaco coal gasification process after cooling and removal of sulfur compounds, has a composition of 36.5 mol% hydrogen, 53.6 mol% carbon monoxide, 8.9 mol% carbon dioxide, 1.0 mol% nitrogen, and less than 0.1 mol% methane and water. Feed stream 499, initially at 74° F. and 750 psia, is heated in heat exchangers 200 and 202 against hot effluent gas streams 505 and 506 from reactor 204. Heated stream 502 contacts powdered methanol synthesis catalyst suspended in an inert liquid in reactor 204. A kinetic model based on the results of earlier laboratory autoclave and pilot plant experiments was used to predict the extent of reaction and methanol production utilizing the commercial methanol synthesis catalyst BASF S3-86 containing copper and zinc oxide on alumina. In these experiments, the catalyst was a powder having a particle size range of 1-10 microns suspended in Drakeol-10 (an inert hydrocarbon oil containing 65 wt % paraffins and 35 wt % aromatics) at a concentration of between about 20 and 50 wt %. The reactor product stream 505, comprising methanol, hydrogen, carbon monoxide, carbon dioxide, and a small amount of vaporized inert liquid, is cooled in exchanger 202 to condense the inert liquid and then is flashed into separator 210. The resulting cooled stream is separated in separator 210 into inert liquid stream 507, which is recycled to the reactor, and crude gaseous product stream 506, which further cooled in exchanger 200 to condense methanol product. Inert liquid makeup is added to separator 210 as needed. Cooled crude product stream 510 is flashed into separator 212, the vapor stream 511 is cooled against cooling water in exchanger 214 and is flashed into separator 216 to yield purge gas stream 514 and crude methanol liquid stream 513. Crude liquid methanol stream 512 from separator 212 and crude liquid methanol stream 513 are flashed into separator 218 to yield purge stream 550 which is used as fuel and final crude methanol stream 551.

The catalyst activity in reactor 204 is controlled by removing spent catalyst and adding fresh catalyst at sufficient rates such that the average catalyst activity in the reactor is 50% of the fresh catalyst activity (catalyst feed and withdrawal lines not shown). Catalyst activity can also be defined as $\eta$, the ratio of average catalyst activity to fresh catalyst activity; in this case $\eta = 0.5$. A catalyst replacement rate of 0.5%/day was selected, which means that 0.5 wt % of the total catalyst inventory is replaced each day. The operating parameters include a space velocity (SV) of 8,000 (std. liters)/(kg. catalyst-hr), a feed rate of 23,000 lb moles/hr, and a reactor pressure of 750 psig. For these operating conditions, feed composition, and average reactor catalyst activity, the optimum reactor temperature to maximize methanol production was found to be about 482° F.; therefore the exothermic heat of reaction is removed by cooling coil 206 in an amount sufficient to control the reactor temperature at 482° F. A heat and material balance for this simulation is given in Table 1 and the reactor performance parameters are summarized as Case 1 in Table 2, which represents the single-stage reactor base case.

TABLE 1

| HEAT AND MATERIAL BALANCE SUMMARY | | | | | | | | | |
|---|---|---|---|---|---|---|---|---|---|
| | Stream Number | | | | | | | | |
| | 499 | 501 | 502 | 504 | 505 | 510 | 514 | 550 | 551 |
| SINGLE REACTOR DESIGN (CASE 1) | | | | | | | | | |
| Pressure (psia) | 800 | | 790 | | 765 | 752 | 742 | 44 | 44 |
| Temperature (deg F.) | 74 | | 380 | | 482 | 182 | 100 | 107 | 107 |
| Composition (mole %) | | | | | | | | | |
| Hydrogen | 35.00 | | 35.00 | | 26.93 | 26.94 | 28.53 | 5.09 | 0.00 |
| Carbon Monoxide | 51.00 | | 51.00 | | 51.21 | 51.24 | 54.22 | 20.79 | 0.02 |
| Carbon Dioxide | 13.00 | | 13.00 | | 14.46 | 14.46 | 15.07 | 60.65 | 1.24 |
| Nitrogen | 1.00 | | 1.00 | | 1.12 | 1.12 | 1.19 | 0.61 | 0.00 |
| Water | 0.00 | | 0.00 | | 0.12 | 0.12 | 0.01 | 0.10 | 2.19 |
| Methanol | 0.00 | | 0.00 | | 6.11 | 6.11 | 0.99 | 12.76 | 96.53 |
| Mineral Oil | 0.00 | | 0.00 | | 0.06 | 0.00 | 0.00 | 0.00 | 0.01 |
| Total Flow (mol/hr) | 23000 | | 23000 | | 20513 | 20498 | 19351 | 57.77 | 1089.40 |
| STAGED REACTOR DESIGN (CASE 2) | | | | | | | | | |
| Pressure (psia) | 800 | 790 | 790 | 765 | 745 | 732 | 723 | 44 | 44 |
| Temperature (deg F.) | 74 | 350 | 380 | 450 | 452 | 203 | 100 | 120 | 120 |
| Composition (mole %) | | | | | | | | | |
| Hydrogen | 35.00 | 35.00 | 35.00 | 28.02 | 21.06 | 21.07 | 23.50 | 3.74 | 0.00 |
| Carbon Monoxide | 51.00 | 51.00 | 51.00 | 51.23 | 51.27 | 51.29 | 57.12 | 19.80 | 0.03 |
| Carbon Dioxide | 13.00 | 13.00 | 13.00 | 14.25 | 15.68 | 15.69 | 16.99 | 57.63 | 1.12 |
| Nitrogen | 1.00 | 1.00 | 1.00 | 1.11 | 1.21 | 1.21 | 1.35 | 0.67 | 0.00 |

TABLE 1-continued

| | HEAT AND MATERIAL BALANCE SUMMARY | | | | | | | |
|---|---|---|---|---|---|---|---|---|
| | Stream Number | | | | | | | |
| | 499 | 501 | 502 | 504 | 505 | 510 | 514 | 550 | 551 |
| Water | 0.00 | 0.00 | 0.00 | 0.12 | 0.08 | 0.08 | 0.00 | 0.05 | 0.80 |
| Methanol | 0.00 | 0.00 | 0.00 | 5.27 | 10.66 | 10.66 | 1.04 | 18.09 | 98.05 |
| Mineral Oil | 0.00 | 0.00 | 0.00 | 0.00 | 0.04 | 0.00 | 0.00 | 0.00 | 0.01 |
| Total Flow (mol/hr) | 23000 | 23000 | 23000 | 20806 | 18972 | 18963 | 16986 | 118.19 | 1858.37 |

TABLE 2

| OPERATING MODE COMPARISONS (CO-rich gas, 750 psig) | | | | | |
|---|---|---|---|---|---|
| | Space Velocity (Std l/hr - kg cat) | | Temperature (°F.) | | Product Conversion, (Mole Methanol per | Relative Catalyst |
| Case | Stage 1 | Stage 2 | Stage 1 | Stage 2 | 100 Moles Feed) | Consumption |
| 1 | 8000 | — | 482 | — | 5.3 | 2 |
| 2 | 8000 | ~7000 | 482 | 452 | 8.6 | 1 |
| 3 | 4000 | — | 482 | — | 6.6 | 1 |
| 4 | 4000 | — | 482 | — | 7.1 | 2 |
| 5 | 8000 | ~7000 | 482 | 482 | 7.3 | 1 |
| 6 | 8000 | ~7000 | 482 | 482 | 7.9 | 2 |
| 7 | 8000 | ~7000 | 482 | 452 | 9.1 | 2 |

Figure 3:
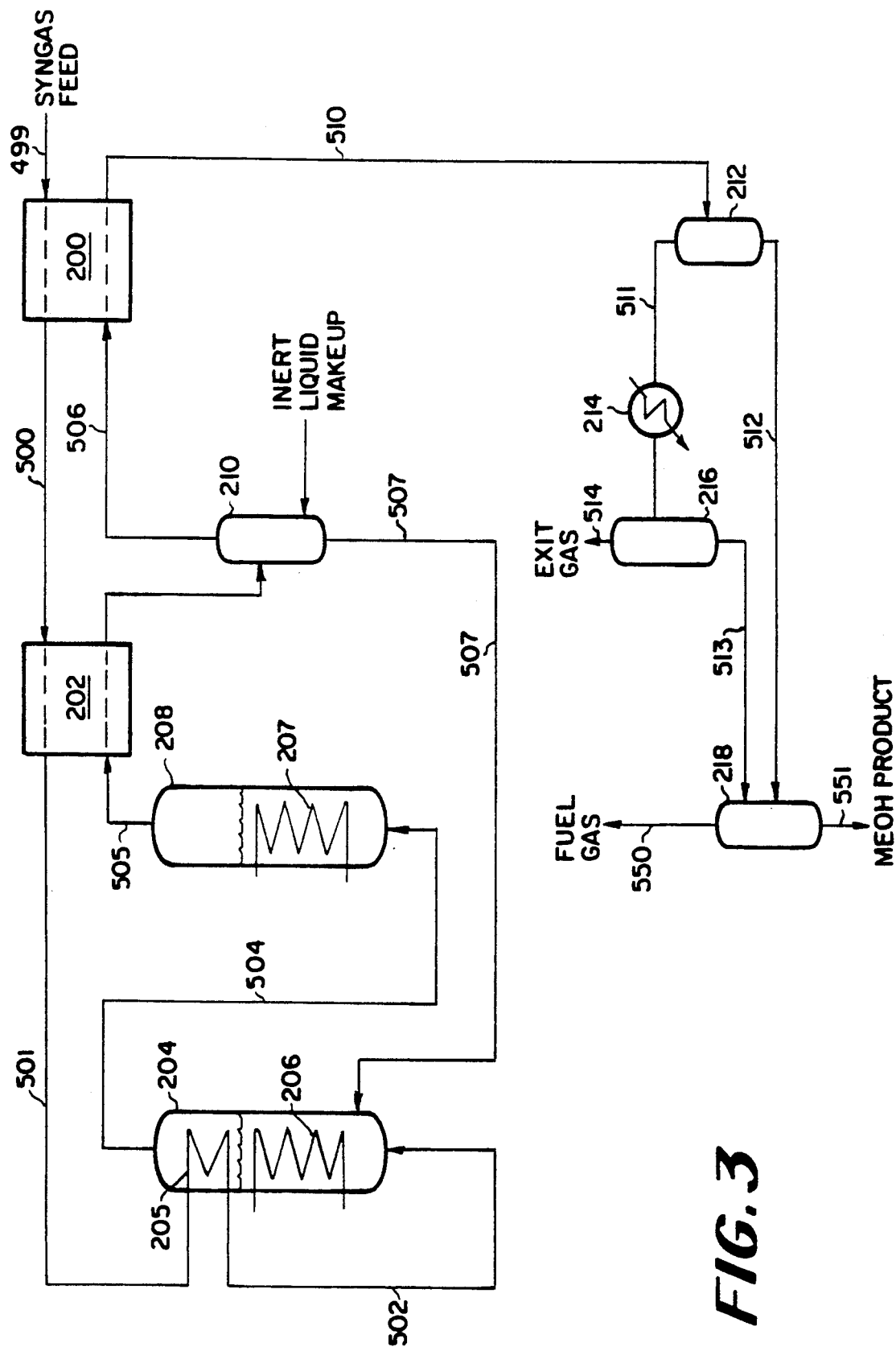
FIG. 3 is a simplified flow diagram for the process of the present invention.

A second process simulation was carried out for a two-stage liquid phase reactor system shown schematically in FIG. 3. This system is identical to the single-stage system of FIG. 2 except for the addition of second stage reactor 208 with cooling coil 207, the addition of feed gas preheat exchanger 205 located in the freeboard of reactor 204, and the catalyst addition/withdrawal procedure. The synthesis gas feed composition, pressure, and temperature are identical to those used in the single-stage process. The first stage reactor pressure is 750 psig, and second stage reactor pressure is 730 psig. Heat is removed by exchanger 205 and cooling coil 206 in a sufficient amount to control the temperature in first stage reactor 204 at 482° F. as in Example 1. In addition, the feed rate and space velocity in the first stage reactor are identical to those in the single-stage reactor of FIG. 2. The space velocity in the second stage reactor depends upon the degree of conversion in the first stage reactor and varies between 7,000 and 7,400 std. liters/(kg. catalyst-hr) for the various simulation cases studied. Fresh catalyst is added to the second stage reactor and partially spent catalyst is withdrawn therefrom to maintain an average reactor catalyst activity at 80% of the fresh catalyst activity, or $\eta = 0.8$. The partially spent catalyst from the second reactor is transferred to the first stage reactor and spent catalyst is withdrawn from the first stage reactor (catalyst addition and withdrawal lines not shown). A catalyst replacement rate of 0.5%/day was selected, which means that 0.5 wt % of the total catalyst inventory in each reactor is replaced each day. The catalyst deactivation rate in the first stage reactor, which is a function of reactor temperature and feed gas composition as discussed earlier, is such that the average reactor catalyst activity is 40% of the fresh catalyst activity, or $\eta = 0.4$. For the operating conditions, feed composition, and average reactor catalyst activity in the second stage reactor 208, the optimum reactor temperature to maximize methanol production was found to be about 452° F. The exothermic heat of reaction is removed by cooling coil 207 in an amount sufficient to control the reactor temperature at 452° F. A heat and material balance for this simulation is given in Table 1 and the reactor performance parameters are summarized as Case 2 in Table 2. This represents the preferred mode of the present invention.

Several additional simulations were carried out at other process conditions for comparison with the base case (Case 1) and the preferred mode (Case 2). Process conditions for these additional simulations are summarized below:

Case 3 single-stage reactor operated with twice the catalyst inventory of Case 1

Case 4 single-stage reactor operated at twice the catalyst replacement rate of Case 3

Case 5 two-stage system similar to Case 2 but operated at 482° F. in the second stage Case 6 two-stage system operated at twice the catalyst replacement rate of Case 5

Case 7 two-stage system operated at twice the catalyst replacement rate of Case 2

The results of these simulations are summarized in Table 2 and lead to several important conclusions regarding the preferred mode of the invention (Case 2). First, a comparison of Case 2 with Case 1 demonstrates the significant benefits of staged operation, namely, a 62% increase in product conversion at half the catalyst consumption. Second, a comparison of Case 2 with Case 5 illustrates the benefit of an optimum second stage temperature, specifically an 18% improvement in product conversion for Case 2 vs Case 5 at the same catalyst consumption. Third, a comparison of Case 6 with Case 5 shows that doubling the catalyst consumption rate results in a relatively small 7.6% increase in product conversion. Finally, a comparison of Case 7 with Case 2 demonstrates that even with an optimum second stage temperature, doubling the catalyst consumption rate yields a small 5.8% increase in product conversion.

EXAMPLE 2

Further simulations were carried out using the same catalyst, inert liquid, catalyst slurry concentration, feed gas composition, pressure, and reactor space velocities as in the preferred mode of Case 2 above. Methanol productivity was predicted utilizing the kinetic model of Example 1 as a function of temperature for typical relative catalyst activities in the first and second stages, and the results are plotted in FIG. 4. The relative catalyst activity, $\eta$, was set at 0.5 for the first stage reactor and at 0.8 or 0.94 for the second stage reactor. FIG. 4 illustrates the key feature of the present invention, namely, that the relationship between temperature and methanol productivity is distinctly different for each reactor stage. As a result, the optimum temperature range which maximizes methanol productivity is distinctly different for each reactor stage. Each optimum temperature is a complex function of relative catalyst activity, synthesis gas feed composition, interstage gas composition, and temperature. For the specific conditions of these simulations, the optimum temperature in the first stage is about 495° F. and in the second stage is about 450° F. Higher catalyst activity reduces the optimum second stage temperature as shown by comparing the second stage curve at $\eta=0.94$ with the curve at $\eta=0.8$.

EXAMPLE 3

Additional simulations were carried out to determine the effects of pressure and feed gas composition on methanol production for single-stage and two-stage reactor systems. The other operating parameters were the same as Example 1. Three feed gas compositions were used—the CO rich gas of Examples 1 and 2, a balanced gas from a steam-methane reformer having stoichiometric concentrations of CO and hydrogen, and synthesis gas from a Lurgi gasifier which has undergone shift and $CO_2$ removal. The compositions of these three feed gases are given in Table 3.

TABLE 3

| | Feed Gas Compositions (Mole %) | | |
|---|---|---|---|
| | CO Rich | SMR Balanced | Shifted Lurgi ($CO_2$ Removed) |
| Hydrogen | 35 | 54 | 60 |
| CO | 51 | 23 | 21 |
| $CO_2$ | 13 | 2 | 1 |
| $N_2$ | 1 | 21 | 1 |
| Methane | 0 | 0 | 17 |

The results of the additional simulations are given in Table 4. The methanol production is given in tons/day in the final reactor effluent and the final methanol product stream (streams 505 and 551 respectively in FIGS. 2 and 3). Recovery is defined as the percent of methanol in the reactor effluent stream 505 which is recovered in final product stream 551.

TABLE 4

EFFECTS OF FEED GAS COMPOSITION AND PRESSURE ON REACTOR PERFORMANCE

| Gas | First Stage Pressure (psig) | No. of Stages | Methanol Production (Tons per Day) Reactor Prod. | Final Prod. | Methanol Recovery (%) |
|---|---|---|---|---|---|
| CO-rich | 750 | 1 | 468 | 404 | 86 |
| | | 2 | 759 | 681 | 90 |
| | | Increase | 62% | 69% | |
| | 1000 | 1 | 611 | 540 | 87 |
| | | 2 | 946 | 869 | 92 |
| | | Increase | 55% | 61% | |
| Balanced | 750 | 1 | 469 | 412 | 88 |
| | | 2 | 794 | 739 | 92 |
| | | Increase | 69% | 80% | |
| | 1000 | 1 | 625 | 577 | 88 |
| | | 2 | 1023 | 968 | 93 |
| | | Increase | 64% | 68% | |
| Shifted Lurgi, | 750 | 1 | 427 | 358 | 84 |
| | | 2 | 737 | 671 | 91 |
| $CO_2$ removed | 1000 | Increase | 73% | 88% | |
| | | 1 | 571 | 513 | 90 |
| | | 2 | 962 | 902 | 94 |
| | | Increase | 68% | 76% | |

The results of these simulations show that two-stage operation increases methanol productivity compared with single-stage operation for all feed gas compositions and pressures used. It is also seen that two-stage operation increases product recovery in all cases, and this occurs for two reasons. First, there is less methanol loss in the unreacted synthesis gas stream 514 for the two-stage system because the flow rate of stream 514 is 13% less than the corresponding stream 514 in the single-stage system. Second, the methanol concentration in the final reactor effluent stream 505 is higher for the two-stage operation than the single-stage operation, which allows higher product recovery.

In an alternate mode of the invention as discussed earlier, the liquid phase methanol process is integrated with a coal gasification combined cycle (CGCC) power generation system. Raw synthesis gas containing hydrogen, carbon monoxide, carbon dioxide, and various impurities is produced by a known coal gasification process such as the Texaco process. Impurities including particulates and sulfur-containing compounds are removed from the raw synthesis gas using any of the various known gas purification processes to yield a purified synthesis gas feed. A portion of the purified synthesis gas feed flows to the two-stage liquid phase methanol process which is operated on a once-through basis as earlier described. Unreacted synthesis gas and crude methanol are recovered from the second stage reactor effluent gas; the unreacted synthesis gas and the remaining portion of the purified synthesis gas feed are used as fuel for a gas turbine-driven electric generator which is part of the CGCC power generation system. The crude methanol is stored and used at least in part as a peak shaving fuel for the gas turbine. Heat integration between the two-stage methanol synthesis process and the CGCC system is accomplished by utilizing the heat of the methanol synthesis reaction to generate steam in each of the reactor stages; the steam is sent to the combustor of the gas turbine-driven electric generator. Alternately, the steam can be sent to one of the CGCC steam systems which provides utility steam to various locations in the plant or to the steam turbine which drives another electric generator. Since the exothermic heats of reaction for the methanol synthesis reactions are higher than the heats of reaction for competing reactions such as water gas shift, maximizing methanol productivity also maximizes the amount of heat energy recovered as steam from the two reactor cooling exchangers 118 and 124 in FIG. 1. In addition, since the molar heat of combustion of methanol is about three times that of hydrogen or CO, the amount of energy available through combustion of the unreacted synthesis gas (streams 75, 78, and 81 in FIG. 1) and the combustion of the total crude methanol (stream 80) is maximized when the reactors are operated at the optimum temperatures.

Catalyst utilization is improved by staged operation in which fresh catalyst is added to the second stage reactor, partially spent catalyst is transferred from the second stage to the first stage reactor, and spent catalyst is removed from the first reactor. The average catalyst activity can be maintained at a high level in the second stage reactor because the first stage reactor removes most of the catalyst poisons present in the feed synthesis gas, and this higher catalyst activity allows the second stage reactor to operate at a lower temperature which reduces the degree of catalyst deactivation due to sintering. In addition, the operation of the second stage reactor at a lower temperature reduces the loss of inert oil in the methanol product thus reducing makeup oil cost and yielding a higher purity methanol product. Another distinguishing feature of the present invention over prior art staged methanol synthesis processes is that the first stage reactor effluent flows directly into the second stage reactor without the need for intermediate product recovery. This differs from the staged reactor system of the earlier cited U.S. Pat. No. 4,766,154 in which methanol product is recovered from the first stage effluent and the remaining unreacted synthesis gas is the feed to the second stage reactor.

Thus the present invention is a two-stage liquid phase process capable of producing methanol from a wide range of synthesis gas compositions wherein methanol productivity, methanol recovery, and catalyst utilization are significantly higher than prior art processes. Optimum temperatures in each stage are selected to maximize methanol productivity for a given feed gas composition, type of catalyst, average catalyst activity, reactor space velocity, and reactor pressure. Operation of the reactors at these optimum temperatures also maximizes the total amount of available energy produced by the two-stage reactor system (operating in a once-through mode) for use elsewhere, preferably in the CGCC power generation system as discussed earlier.

The essential characteristics of the present invention are described fully and completely in the foregoing disclosure, from which one skilled in the art can understand the invention and make various changes and modifications thereto without departing from the basic spirit and scope thereof.

I claim:

1. A process for the production of methanol from synthesis gas feed containing hydrogen, carbon monoxide, and carbon dioxide comprising:
    (a) introducing said synthesis gas feed into a first liquid phase reactor containing solid methanol synthesis catalyst in an inert liquid;
    (b) reacting said synthesis gas in the presence of said catalyst in said first liquid phase reactor to produce methanol;
    (c) withdrawing an effluent gas stream comprising methanol, hydrogen, carbon monoxide, and carbon dioxide from said first liquid phase reactor and introducing said effluent gas stream into a second liquid phase reactor containing said solid methanol synthesis catalyst in said inert liquid;
    (d) reacting said effluent gas stream in the presence of said catalyst in said second liquid phase reactor to produce additional methanol;
    (e) removing sufficient amounts of heat from said first and second liquid phase reactors to control the respective temperatures therein such that the methanol productivity is maximized for a given composition of said synthesis gas feed and given activities of said catalyst in each of said liquid phase reactors;
    (f) withdrawing a mixed product stream comprising methanol, hydrogen, carbon monoxide, and carbon dioxide from said second liquid phase reactor; and
    (g) withdrawing spent catalyst from said first liquid phase reactor, transferring partially spent catalyst from said second liquid phase reactor to said first liquid phase reactor, and introducing fresh catalyst into said second liquid phase reactor.

2. The process of claim 1 which further comprises heating said synthesis gas feed by indirect heat exchange with said mixed product stream.

3. The process of claim 2 which further comprises additional heating of said synthesis gas feed by indirect heat exchange with said effluent gas stream.

4. The process of claim 1 wherein said mixed product stream contains a vaporized portion of said inert liquid, and wherein said mixed product stream is cooled and separated into (1) a condensed inert liquid stream which is recycled to said first and second liquid phase reactors, and (2) a final mixed product stream essentially free of said inert liquid.

5. The process of claim 1 which further comprises cooling and partially condensing said mixed product stream and separating the resulting partially condensed stream into a crude methanol liquid product and a stream of unreacted synthesis gas components comprising hydrogen, carbon monoxide, and carbon dioxide.

6. The process of claim 1 wherein said heat is removed from each of said first and second liquid phase reactors by indirect heat exchange with a cooling fluid flowing through individual exchangers located within each of said reactors.

7. The process of claim 6 wherein said cooling fluid is selected from the group consisting of said synthesis gas feed, steam, and boiler feed water.

8. The process of claim 1 wherein said first liquid phase reactor is operated at a temperature between about 455° F. and 535° F.

9. The process of claim 8 wherein said first liquid phase reactor is operated at a temperature between about 475° F. and 515° F.

10. The process of claim 8 wherein said second liquid phase reactor is operated at a temperature between about 415° F. and 475° F.

11. The process of claim 10 wherein said second liquid phase reactor is operated at a temperature between about 425° F. and 465° F.

12. The process of claim 1 wherein water is added to said synthesis gas feed prior to said first liquid phase reactor.

13. The process of claim 1 wherein carbon dioxide is added to said synthesis gas feed prior to said first liquid phase reactor.

14. The process of claim 1 wherein water is added to said effluent gas stream prior to said second liquid phase reactor.

* * * * *

UNITED STATES PATENT AND TRADEMARK OFFICE
CERTIFICATE OF CORRECTION

PATENT NO. : 5,179,129
DATED : January 12, 1993
INVENTOR(S) : David William Studer It is certified that error appears in the above-identified patent and that said Letters Patent is hereby corrected as shown below:

Column 1, line 3, after the title, insert the following paragraph:

This invention was made with Government support under Contract No. DE-AC22-87PC90005 between Air Products and Chemicals, Inc., and the U.S. Department of Energy. The Government has certain rights in this invention.

Signed and Sealed this

Twenty-eighth Day of October, 1997

Attest:

BRUCE LEHMAN

Attesting Officer

Commissioner of Patents and Trademarks